(12) United States Patent
Noland

(10) Patent No.: US 10,596,607 B2
(45) Date of Patent: Mar. 24, 2020

(54) BIOREMEDIATION COMPOSITION WITH TIME-RELEASE MATERIALS FOR REMOVING ENERGETIC COMPOUNDS FROM CONTAMINATED ENVIRONMENTS

(71) Applicant: REMEDIATION PRODUCTS, INC., Golden, CO (US)

(72) Inventor: Scott Noland, Arvada, CO (US)

(73) Assignee: REMEDIATION PRODUCTS, INC., Golden, CO (US)

( * ) Notice: Subject to any disclaimer, the term of this patent is extended or adjusted under 35 U.S.C. 154(b) by 94 days.

(21) Appl. No.: 15/954,715

(22) Filed: Apr. 17, 2018

(65) Prior Publication Data

US 2018/0229283 A1 Aug. 16, 2018

Related U.S. Application Data

(62) Division of application No. 15/678,165, filed on Aug. 16, 2017, now Pat. No. 9,950,353.

(60) Provisional application No. 62/377,918, filed on Aug. 22, 2016.

(51) Int. Cl.
| | | |
|---|---|---|
| *B09C 1/10* | (2006.01) | |
| *A61K 31/715* | (2006.01) | |
| *A61K 47/18* | (2017.01) | |
| *A61K 47/26* | (2006.01) | |
| *A61K 47/59* | (2017.01) | |
| *C02F 3/10* | (2006.01) | |
| *B09C 1/00* | (2006.01) | |
| *C02F 1/28* | (2006.01) | |
| *C12N 1/00* | (2006.01) | |
| *C02F 103/06* | (2006.01) | |
| *C02F 101/00* | (2006.01) | |
| *C02F 3/00* | (2006.01) | |

(52) U.S. Cl.
CPC ............ *B09C 1/10* (2013.01); *A61K 31/715* (2013.01); *A61K 47/183* (2013.01); *A61K 47/26* (2013.01); *A61K 47/595* (2017.08); *B09C 1/00* (2013.01); *B09C 1/002* (2013.01); *C02F 1/288* (2013.01); *C02F 3/108* (2013.01); *B09C 2101/00* (2013.01); *C02F 1/281* (2013.01); *C02F 1/283* (2013.01); *C02F 2003/001* (2013.01); *C02F 2101/003* (2013.01); *C02F 2103/06* (2013.01); *C12N 1/00* (2013.01); *Y02W 10/15* (2015.05)

(58) Field of Classification Search
CPC .... A61K 31/715; A61K 47/183; A61K 47/26; A61K 47/595; B09C 1/10; B09C 1/00; B09C 1/002; B09C 2101/00; C02F 3/108; C02F 1/281; C02F 1/283; C02F 1/288; C02F 2003/001; C02F 2101/003; C02F 2103/06; C12N 1/00; Y02W 10/15
See application file for complete search history.

(56) References Cited

U.S. PATENT DOCUMENTS

| | | | |
|---|---|---|---|
| 5,458,861 A * | 10/1995 | Buchanan | B01D 53/04 423/244.01 |
| 5,593,888 A | 1/1997 | Glaze et al. | |
| 5,855,946 A | 1/1999 | Seib et al. | |
| 6,280,770 B1 * | 8/2001 | Pather | A61K 9/0007 424/464 |
| 6,348,639 B1 | 2/2002 | Crawford et al. | |
| 2005/0006306 A1 | 1/2005 | Noland et al. | |

* cited by examiner

*Primary Examiner* — Deborah K Ware
(74) *Attorney, Agent, or Firm* — Snell & Wilmer L.L.P.; Kent A. Lembke

(57) ABSTRACT

A composition useful for removing energetic compounds from contaminated environments. The composition includes a supported reactant including an adsorbent with high affinity for energetic compounds. Further, the composition includes a first bioremediation material comprising at least one organism capable of degrading an energetic compound and a polymeric substance fueling the first bioremediation material during the degrading of the energetic compound. Additionally, the composition includes a second bioremediation material breaking the polymeric substance into smaller molecules over a degradation time period to provide the fueling of the first bioremediation material in a time-release manner.

20 Claims, 1 Drawing Sheet

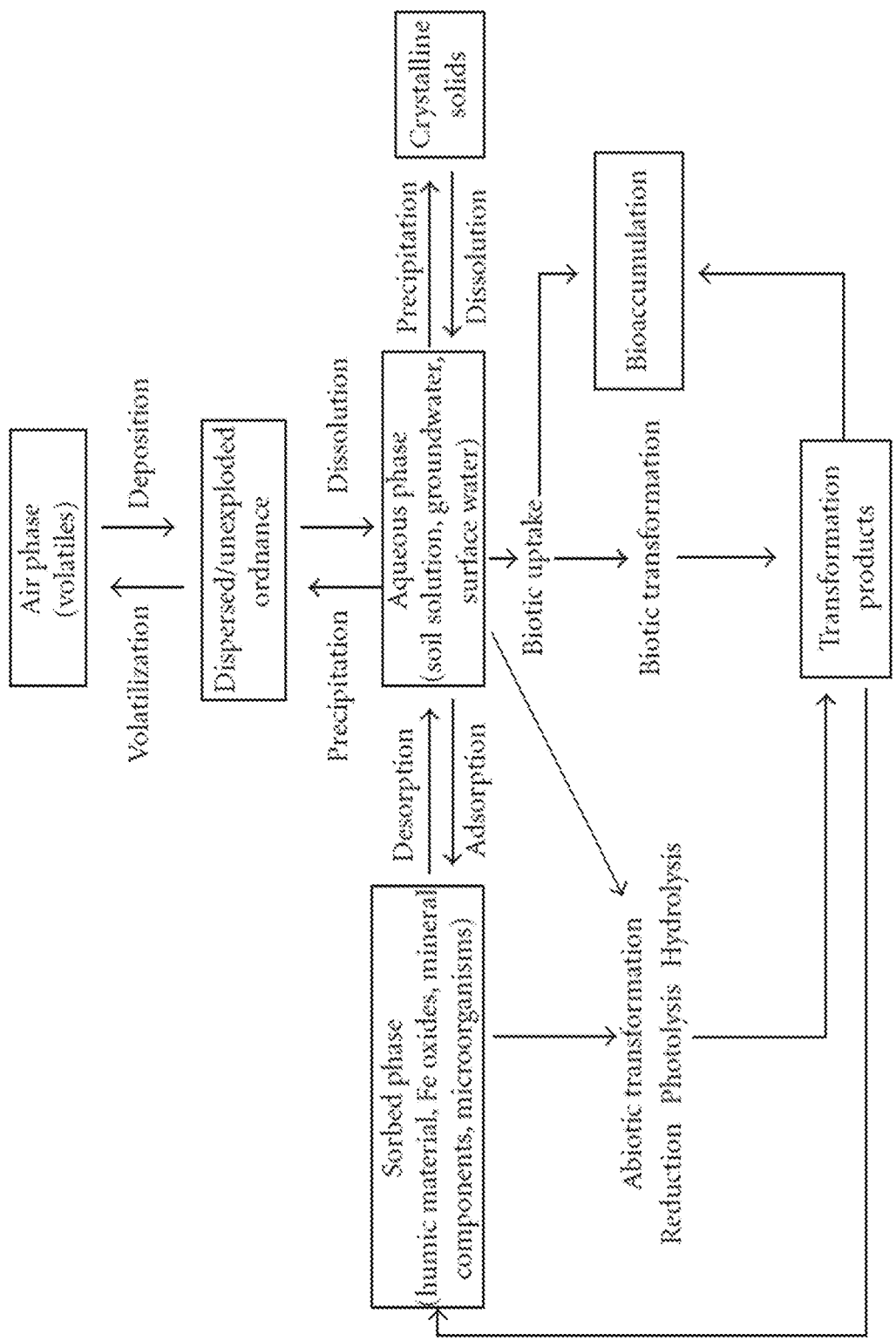

BIOREMEDIATION COMPOSITION WITH TIME-RELEASE MATERIALS FOR REMOVING ENERGETIC COMPOUNDS FROM CONTAMINATED ENVIRONMENTS

CROSS REFERENCE TO RELATED APPLICATIONS

This application is a divisional application of U.S. patent application Ser. No. 15/678,165, filed on Aug. 16, 2017, which claims priority to U.S. Provisional Pat. Appl. No. 62/377,918, filed Aug. 22, 2016, both of which are incorporated herein by reference in their entireties.

BACKGROUND

Energetic compounds, defined as the active chemical components of explosives and propellants, are necessary for a variety of purposes spanning peaceful and military applications. Common energetic compounds include the explosives 2,4,6-trinitrotoluene (TNT), hexahydro-1,3,5-trinitro-1,3,5-triazine (RDX), and octahydro-1,3,5,7-tetranitro-1,3,5,7-tetrazocine (HMX) as well as nitroglycerin (NG), nitroguanidine (NQ), nitrocellulose (NC), 2,4-dinitrotoluene (DNT), and various perchlorate formulations employed in missile, rocket, and gun propellants. The present description is not limited to just these compounds and may generally be applied to the wide range of nitrocompounds detailed on the "List of Explosive Materials" published in the Federal Register by the Bureau of Alcohol, Tobacco, Firearms, and Explosives.

For decades, the United States military used unlined evaporation/percolation lagoons for disposal of wastewaters from manufacturing, demilitarization, and load, assemble, and pack (LAP) operations. Many explosives have subsequently accumulated at the surfaces of lagoons, sometimes at concentrations in the percent range. These areas are a significant concern relative to long-term soil and groundwater contamination as well as for the potential for accidental detonation. Additionally, energetic materials or compounds have contaminated soils worldwide as the result of manufacturing operations, military conflict, and military training activities. Explosives such as trinitrotoluene (TNT), cyclonite (RDX), and octogen (HMX) and propellants such as nitrate esters (e.g., NG or the like) and perchlorates present the greatest concern to public health and the environment because they are manufactured and used in the greatest quantities. Unfortunately, RDX, TNT, and perchlorate are common groundwater contaminants throughout North America. In addition, many of the degradation products stemming from these compounds also pose health and environmental hazards.

Energetic compounds undergo varying degrees of chemical and biochemical transformation depending on the compounds involved and environmental factors. For example, processes that influence the environmental fate of explosive compounds may be divided into the following categories: (1) influences on transport (dissolution, volatilization, and adsorption); and (2) influences on transformation (photolysis, hydrolysis, reduction, and biological degradation).

FIG. 1 illustrates the major fate and transport pathways for energetic materials. It is clear from FIG. 1 that a complex range of degradation products are possible when these compounds are released to the environment. The typical site is contaminated with multiple energetics or energetic compounds resulting in a vast array of transformation products, which may be toxic and result in health and environmental hazards. Many of the transformation pathways shown in FIG. 1 have been exploited to develop technology for remediation of energetics based contamination in soil and groundwater.

SUMMARY

The inventor recognized that the largest limitation of these prior remediation technologies is that the contaminants are not fully transformed to non-toxic materials so remediation often results in exchanging one toxin for another. From a regulatory point of view, very little improvement is realized, considerable financial resources are wasted with little benefit, and health hazards remain when these conventional technologies are implemented. Also, due to the relatively low aqueous solubility of many explosives such as TNT (i.e., 130 mg/L), RDX (i.e., 42 mg/L), and HMX (i.e., 5 mg/L), slow dissolution of solid particles results in continuous release to the local environment over extended periods of time.

Granular activated carbon (GAC) is one of the most widely used materials for treating groundwater and wastewater contaminated with explosives, but no permanent treatment is achieved. Bioregeneration, which treats adsorbed contaminants by desorption and biodegradation, is being developed as a method for reducing GAC usage rates and permanently degrading RDX and HMX. In addition, carbon has been shown to be an effective medium to shuttle electrons (produced from biological degradation of donor substrates) to absorbed energetics and facilitate its degradation. These processes are being developed to reduce the GAC usage rate and extend the life of carbon beds.

Most explosives that occur as groundwater pollutants are nitro aromatic compounds (TNT, trinitrobenzene, and various di- and mono-nitrotoluenes) or nitramines (RDX, HMX, and Tetryl). Under favorable conditions, most of these compounds react rapidly with zero-valent iron (ZVI), which suggests that permeable reactive barriers containing zero-valent iron (Fe-PRBs) might be useful for remediation of groundwater contaminated with explosives. Much work along these lines has been completed over the last ten years, and ZVI has been widely used for remediation of groundwater. The problem with using ZVI in remediating energetic compounds including explosives is two-fold: (1) although parent compounds such as TNT are rapidly removed from groundwater, it is believed that a portion of the original TNT along with degradation byproducts are sorbed to the oxidized iron surface and it is not clear how stable the sorption will be over time; and (2) reduced byproducts including triaminotoluene are formed that are also very toxic. In effect, existing technologies using ZVI are effectively exchanging one toxin for another.

In addition to abiotic methods such as the use of ZVI, energetics have also been remediated using biological technologies. Certain strains of pseudomonas and fungi can use TNT as a nitrogen source through the removal of nitrogen as nitrite from TNT under aerobic conditions and the further reduction of the released nitrite to ammonium, which is incorporated into carbon skeletons. Phanerochaete chrysosporium and other fungi mineralize TNT under ligninolytic conditions by converting it into reduced TNT intermediates, which are excreted to the external milieu, where they are substrates for ligninolytic enzymes. Most, if not all, aerobic microorganisms reduce TNT to the corresponding amino derivatives via the formation of nitroso and hydroxylamine intermediates. Condensation of the latter compounds yields highly recalcitrant azoxytetranitrotoluenes.

Anaerobic microorganisms can also degrade TNT through different pathways. One pathway involves reduction of TNT to triaminotoluene, but subsequent steps are still not known. Some such species may reduce TNT to hydroxylaminodinitrotoluenes, which are then further metabolized. Another pathway has been described that involves nitrite release and further reduction to ammonium, with almost 85% of the N-TNT incorporated as organic N in the cells. It was recently reported that in this strain TNT can serve as a final electron acceptor in respiratory chains and that the reduction of TNT is coupled to ATP synthesis. A number of biotechnological applications of bacteria and fungi, including slurry reactors, composting, and land farming, have also been discussed for removing TNT from polluted soils. These treatments have been designed to achieve mineralization or reduction of TNT and immobilization of its amino derivatives on humic material. These approaches are highly efficient in removing TNT, and increasing amounts of research into the potential usefulness of phytoremediation, rhizophytoremediation, and transgenic plants with bacterial genes for TNT removal are being completed.

The inventor discovered that the above-described technologies share one or more of the following drawbacks: (1) long periods of time are required for sustained reduction in contaminant concentrations to be realized; (2) although reductions can be realized, regulatory cleanup standards or goals for soil and groundwater are seldom attained; (3) performance is inconsistent and highly dependent on site conditions and contaminant levels; and (4) treatment technologies such as ZVI or biodegradation are often effective with specific explosives but only partially effective with others. For example, with the use of these technologies, by-products are often released that are more toxic than the original contaminants, and this release creates a transient condition more egregious than what existed before treatment. Hence, the inventor has identified an ongoing need for remediation processes to effectively clean up soil and/or groundwater contaminated with energetics or energetic compounds that is rapid, is cost effective, and does not release toxic by-products into the soil, air, or groundwater.

In brief, the present description provides compositions and methods for in situ soil and/or groundwater remediation that can reduce contaminant concentrations quickly to regulatory cleanup standards. The compositions and methods work in a variety of soil and groundwater conditions and are applicable for the remediation of a variety of contaminants. The methods and compositions of this description do not release toxic by-products into the soil, groundwater, or air and have no adverse impact on soil properties or groundwater quality. The compositions of this description are also cost effective in that they remain active for an extended period of time so that only a single treatment is required.

In prior work, the inventor created a composition which, when added to a site such as soil and/or groundwater contaminated with one or more halogenated hydrocarbons, adsorbs the halogenated hydrocarbons and reduces them to less innocuous by-products. This composition was a granular activated carbon whose inner pore structure had been impregnated with elemental iron. This elemental iron-based composition may be considered a supported reactant for in situ remediation of soil and/or groundwater contaminated with one or more halogenated hydrocarbon. The supported reactant was formed mainly of an adsorbent impregnated with zero valent iron, and the adsorbent was chosen so as to be capable of adsorbing the halogenated hydrocarbon contaminants as well as the intermediate by-products resulting from the degradation of the contaminants. In one embodiment, the adsorbent is activated carbon. The inventor determined that this elemental iron-based composition was useful in methods for the remediation of an environment contaminated with halogenated hydrocarbons, with such methods including adding the supported reactant to one or more sites of the contaminated environment. In this manner, reductive dehalogenation of the halogenated hydrocarbon contaminants is achieved.

In regard to the present description, the inventor further recognized there may be a useful synergy between this elemental iron-based composition and bioremediation technologies. Particularly, it was understood that successful degradation of many contaminants is often mainly about achieving successful electron transfer. To this end, the elemental iron-based composition may be used with a first blend of organisms that are chosen for their ability to degrade explosives, other energetic compounds, and their degradation byproducts. For example, the elemental iron-based composition may act to absorb the contaminants within the pores of the activated carbon near the impregnated iron, which acts in conjunction with this first blend of organisms to degrade the contaminants.

With respect to the supported reactant, this same synergy may also exist when metallic iron is replaced with other metals, alloys, or multimetal combinations. For example, zinc, tin, platinum, palladium, copper, manganese, iridium, cobalt, titanium, or nickel may perform better than iron for degrading energetic compounds. In addition, alloys such as magnesium-aluminum or ferro-titanium may offer advantages. Finally, bimetallic combinations like copper plated iron, or iron activated with platinum or palladium may prove effective.

Further, though, the inventor recognized that it is desirable to "feed" or "fuel" the organisms of the first blend/composition to continue to degrade the contaminants over a longer period of time. Prior substrates used for this purpose often were ineffective as they donate hydrogen or the like very quickly and do not continue to be effective in feeding or fueling the first blend of organisms over time (e.g., over 20 to 40 days or more).

To this end, the inventor discovered that it would be useful to provide a combination of an organic compound (or polymeric substance or polymer) such as a complex carbohydrate to fuel/feed the first blend of organisms and a second blend of organisms whose sole purpose/function is to break the organic compound(s) into smaller molecules that are more readily utilized by the microorganisms of the first blend to support degradation of the contaminants. In this way, the fuel or smaller molecules from the substrate are made available in a time released manner (e.g., the organic compound with the organisms acts as a time release material) that facilitates the degradation of the contaminants over a much longer period of time so as to achieve greater percentages of degradation (e.g., 64 to 86 percent degradation achieved in some bench trials). In particular implementations, the organic compound is a complex carbohydrate that is (or includes) starch (such as a food grade starch from a source such as corn, starch, rice, wheat, or the like) while other exemplary, but not limiting, implementations utilize chitin.

BRIEF DESCRIPTION OF THE DRAWINGS

FIG. 1 is functional block and/or flow diagram illustrating the major fate and transport pathways for energetic materials.

DETAILED DESCRIPTION

The following description relates to new remediation compositions and methods for in situ remediation of environments such as soil or groundwater contaminated with energetics/explosives. The description builds upon prior discoveries made by the inventor of a supported reactant (or elemental iron-based composition) that is particularly well suited for cleaning up soil and groundwater contaminated with a variety of organic toxins. The effectiveness of this supported reactant/elemental iron-based composition is greatly enhanced, though, by combining it with bioremediation technologies (e.g., a set or blend of one-to-many microorganisms) suited for degrading these toxins to create a new remediation composition.

Further, the effectiveness of the bioremediation technologies is increased by including in the new remediation composition a combination of a time release material (or organic compound or polymeric substance (such as a complex carbohydrate (e.g., starch, chitin, or the like) with a second set or blend of one or more microorganisms chosen for breaking up or degrading the time release material (e.g., a complex carbohydrate) into smaller molecules for better utilization over time by the second set or blend of microorganisms. Stated differently, the elemental iron-based composition (or supported reactant as called herein) combined with the organic compound(s) or polymeric substance(s) (e.g., a starch (or other complex carbohydrate)) and microorganisms degrading organic compounds/polymeric substances provide a time release composition or platform that acts to enhance and support (e.g., fuel) the degradation over a relatively long period (e.g., 20 to 365 days or more). This time release platform is used (as it slowly releases hydrogen or the like) in the new composition described herein by the set or blend of microorganisms included that degrade the contaminants such as energetic compounds including explosives.

With regard to "the time release material" to be used, the inventor understood that polymers are large molecules formed when monomers link together to form the larger molecule. The monomer can be a simple compound like ethylene ($CH_2CH_2$) or a more complex substance or material such as a sugar. In general, polymers have the following structure: [repeating unit]$_n$, where the repeating unit is a monomer and n is the degree of polymerization. With respect to degradation of halogenated organic compounds, many simple substances have been used to promote such degradation. However, they are typically very short lived and include sugars and fatty acids like lactic acid. As previously described, these simple substances or compounds are water soluble and readily consumed by a variety of microorganisms.

With this problem in mind, the inventor recognized the need for a time release material that would be a source of such compounds that play the role of a substrate that can be beneficially used by organisms capable of degrading explosive compounds. Specifically, the inventor discovered that organic compounds or polymeric substances (or polymers) were good sources of such time released materials. Naturally occurring polymers may be preferred in some applications, but manmade polymers may also be used to practice remediation products/processes of the present description.

Naturally occurring polymers fall into three general types or categories: (1) polynucleotides; (2) polyamides; and (3) polysaccharides. Of these, the inventor discovered through extensive research and experimentation that polyamides and polysaccharides are likely the most applicable and useful. In some specific embodiments, one of the more effective polymeric substances or organic compounds presented in this description is complex carbohydrates such as one or more starches (which are polysaccharides). Polymers contain monomeric units that can fulfill the role of a time release material, which is beneficially used to support degradation of explosive compounds. Polymeric fatty acids such as polylactic acid and polymers of amino acids (polyamides) are additional examples of organic compounds or polymeric substances that may be utilized. Short chains of amino acids with 6 to 30 acids linked together by peptide bonds are referred to as polypeptides. When the number of amino acids reaches 40 or more (molecular weight of 5000 Da (Daltons)), the chain takes on the properties associated with proteins. Examples of proteins that may be used in the remediation compositions include casein, yeast extract, and peptone.

In general, polymeric substances that can be used as part of the remediation compositions described and claimed herein include organic compounds, which typically will include monomeric units that can be used as a time release material supporting the degradation of explosive organic compounds with average molecular weight exceeding 2500 AMU or more preferably exceeding 5000 Da. Polysaccharides may alternatively be characterized according to the general formula $C_x(H_2O)_y$, where x is an integer greater than 12 and preferably where x is an integer between 200 and 2500 and further where x and y are different integers. Alternatively, polysaccharides may be characterized according to the general formula $(C_6H_{10}O_5)_n$, where n is an integer that, in one embodiment, is greater than or equal to 40 and less than or equal to 3000.

This description provides specific examples of polymeric substances and/or organic compounds in the form of complex carbohydrates such as food grade starch. However, it will be understood by those skilled in the art that these are non-limiting examples and other organic compounds or polymeric substances may be substituted in these remediation compositions. The description also discusses the supported reactant or elemental iron-based composition that is included in the new remediation composition, which is useful for decontaminating soil and/or groundwater. The description then proceeds to detail possible mixtures or "recipes" for providing the new remediation composition.

More specifically, the remediation composition may include a supported reactant for the reduction of explosives and other energetic compounds. The reactant may consist essentially of an adsorbent impregnated with zero valent iron, and the adsorbent may have an affinity for energetics. In addition, the adsorbent can be chosen so as to be capable of adsorbing toxic intermediate by-products produced by the reduction of the contaminants, e.g., intermediates such as aminodinitrotoluene, diaminitrotoluene, and other intermediate by-products of trinitrotoluene decomposition or those of other energetic compounds. In this way, the adsorbent provides a means for concentrating contaminants into a new matrix where a high surface area of iron is available, as discussed hereinafter in detail. The supported reactants accomplish treatment of explosives in soil and groundwater, at least in part, by degrading nitro contaminants and their toxic intermediate by-products into harmless by-products (e.g., nitrogen, carbon dioxide ($CO_2$), and water, and so on).

The supported reactants are in some implementations prepared using an adsorbent having a high surface area per unit weight and a high affinity for explosives and other energetic compounds. Suitable adsorbents for these purposes include, but are not limited to, activated carbon, vermiculite, alumina, zeolites, and chars such as wood, bone, and the like. Thus, while the method of preparing the supported reactants is described utilizing activated carbon as the adsorbent, it is to be understood that the methods and supported reactants that may be used in the new remediation composition are not limited to only this adsorbent.

In one non-limiting embodiment, the supported reactant consists essentially of activated carbon as the support, and the activated carbon is impregnated with zero valent iron. The activated carbon preferably has a high surface area per unit weight (preferably ranging from 800 to 2000 m$^2$/g) and a high affinity for explosives and other energetic compounds. The ability of activated carbon to adsorb organics from water enhances its utility as a support. However, while the activated carbon can trap these contaminants, carbon by itself is not stable over long periods, i.e., it is subject to erosion, in which case the contaminants move with the activated carbon and are not truly trapped and removed. Activated carbon provides an efficient matrix for adsorption of energetic and explosive contaminants. Impregnating the activated carbon with the zero valent iron provides submicron deposits of iron within the pore structure of the carbon, thus maximizing the metal's available surface area and placing the metal where the concentration of adsorbed contaminant molecules is the highest. Accordingly, the supported reactant allows efficient contact of the iron with adsorbed chemicals contaminants, since the iron will be in close proximity to the contaminant. The supported reactants of the new remediation composition accomplish treatment of energetics in soil and groundwater by degrading these chemicals into harmless by-products.

Activated carbons can be manufactured from a broad spectrum of material including, but not limited to, coal, coconut shells, peat, and wood. The raw material is typically crushed, screened, and washed to remove mineral constituents. The material is then activated at high temperatures (typically over 900° C.) in a controlled atmosphere to produce a material having an extensive porous network and a large surface area (e.g., ranging from 1000 to 2000 m$^2$/g). The supported reactants may be produced with virtually any source of activated carbon. All that is needed are minor adjustments in system design parameters to account for the different forms of carbon. When the product is used for remediation of groundwater, acid-washed carbons may be useful since the acid wash removes any extraneous metals that may be of environmental concern from the carbon.

With activated carbon, available surface areas for adsorption preferably range from about 800 m$^2$/gm to 2000 m$^2$/gm. Some loss of carbon surface area may occur during the impregnation process, but testing has shown that the loss is not significant when measured by adsorption isotherms. In one embodiment, the surface area of the zero valent iron used in the supported reactant included in the remediation composition ranges from about 50 to 400 m$^2$ per gm-deposited iron. The weight percent of iron deposited within the carbon matrix ranges from about 1 percent to 20 percent by weight of iron and, in some useful embodiments, in the range of about 7 to 8 percent by weight of iron. In one embodiment, the supported reactant has a total surface area of over 1500 m$^2$/g. The iron contained in the supported reactants typically is a high purity iron. In other words, the iron does not contain other metals, such as heavy metals, which would contaminate groundwater and drinking water beyond limits allowed by the U.S. Environmental Protection Agency (EPA). Preferably, the iron is at least 99% pure, and the concentrations of trace contaminants such as chromium, aluminum, potassium, cesium, zinc, lead, nickel, cadmium, and/or arsenic are less than 5 ppm. In some cases, the source of the iron is a food grade salt.

In one particular embodiment, a supported reactant used in the remediation composition for in situ remediation of soil and/or groundwater contaminated with energetics (or energetic compounds) includes (or even consists essentially of in some cases): (i) an adsorbent impregnated with zero valent iron and (ii) a metal hydroxide or a metal carbonate (such as limestone) in an amount sufficient to provide a reactant having a pH greater than 7. The adsorbent is selected to be capable of adsorbing explosives and other energetics. Suitable adsorbents for purposes of this invention include, but are not limited to, activated carbon, vermiculite, alumina, and zeolites.

As described above, the contaminants in the soil/ground water being remediated are initially adsorbed by the activated carbon and then degraded through a reduction mechanism. Béchamp iron and acid reduction is a classic example of amination by reduction of nitroaromatics. This well-known chemistry provides at least some basis for exploring the use of iron under mild conditions for reduction of energetics. Although the original process used a strong mineral acid (hydrochloric acid), it was learned that various end products were obtained when pH was varied from acidic to basic conditions and that salts of mineral acids could also be advantageous.

The inventor completed preliminary bench testing with activated carbon impregnated with elemental iron on a range of nitrocompounds including a nitroalkane, a nitroaromatic, and an explosive nitrophenolic to evaluate the range of activity. In addition, testing was carried out at neutral, basic, and acidic pH and with an iron salt at neutral pH as an activator. This preliminary testing did not include the biological components of this new technology and was focused on abiotic activity of the activated carbon/iron platform and its ability to absorb various classes of energetic compounds over a range of pH with metal salt activation and on identifying degradation byproducts. A key feature of the new composition described herein is that contaminants are electrically bound to the microscale deposits of elemental iron partially dissolved into the carbon walls within the microporous structure of the activated carbon to enable shuttling of electrons through the carbon and metal connection to the bound contaminant and effect reduction. The preliminary testing confirmed that this key feature was present and highly active as degradation products were detected in every case.

Preliminary testing has been performed and additional testing is scheduled with the supported reactant coupled to the full complement of microorganisms and time release substrates to fuel complete degradation of these energetic compounds. Based on performance of this new composition with other classes of contaminants including halogenated hydrocarbons, cyclic alkanes, aromatic compounds, alcohols, and ketones, it is anticipated that performance with these explosives and other energetic compounds will be effective and result in complete degradation of the parent and intermediate by-products into non-toxic by-products such as nitrogen, $CO_2$ and water. In addition, it is anticipated that the elemental iron impregnated within the porous structure of the activated carbon will not be consumed and will perform in a true catalytic fashion accelerating the rate of contaminant degradation.

The main focus of this new remediation composition has been the combination of a polymeric substrate with multiple blends of microorganisms designed to degrade targeted energetic contaminants or the polymeric substrate with the supported reactant described in previous sections. However, it must be kept in mind that with respect to some of the contaminants included within the family of energetics and explosives, the supported reactant alone will completely degrade them without the need for inclusion of any substrate or microorganisms. Examples of such compounds include nitroglycerine, nitroguanidine, and perchlorate. Although the use of the combination of supported reactant with substrate and microorganisms might improve the rates of degradation of these compounds, it is not necessary and the iron impregnated activated carbon (supported reactant) will perform exceptionally well on its own.

In review, a composition is taught herein that is useful for removing energetic compounds from contaminated environments. The composition includes a supported reactant including an adsorbent with high affinity for energetic compounds. Further, the composition includes a first bioremediation material comprising at least one organism capable of degrading an energetic compound and a polymeric substance fueling the first bioremediation material during the degrading of the energetic compound. Additionally, the composition includes a second bioremediation material containing at least one organism or material designed to break the polymeric substance into smaller molecules over a degradation time period to provide the fueling of the first bioremediation material in a time-release manner.

In some embodiments of the composition, the adsorbent is impregnated with zero valent iron. In the same and other embodiments, the adsorbent comprises at least one of activated carbon, vermiculite, alumina, a zeolite, or a char. In practice, the energetic compound may be an explosive or a propellant. It may be desirable for the first bioremediation material to include at least one of bacteria, fungi, an aerobic microorganism, an anaerobic microorganism, an algae, a protozoa, or an actinomycetes.

In some preferred embodiments, the degradation time period is at least 20 days in length, and the polymeric substance includes at least one of a polyamide, a polysaccharide, a complex carbohydrate, a polymeric fatty acid, a polymer of an amino acid, and a protein. For example, the polymeric substance comprises at least one of starch and chitin, with some useful compositions using a food grade starch.

I claim:

1. A composition for removing energetic compounds from contaminated environments, comprising:
   a supported reactant including an adsorbent with high affinity for energetic compounds;
   a first bioremediation material comprising at least one organism capable of degrading an energetic compound;
   a polymeric substance fueling the first bioremediation material during the degrading of the energetic compound; and
   a second bioremediation material breaking the polymeric substance into smaller molecules over a degradation time period to provide the fueling of the first bioremediation material in a time-release manner,
   wherein the adsorbent includes a magnesium-aluminum alloy, and
   wherein the degradation time period is at least 20 days in duration.

2. The composition of claim 1, wherein the adsorbent is impregnated with zero valent iron.

3. The composition of claim 1, wherein the adsorbent includes at least one of zinc, tin, platinum, palladium, copper, manganese, iridium, cobalt, titanium, and nickel.

4. The composition of claim 1, wherein the adsorbent includes a ferro-titanium alloy.

5. The composition of claim 1, wherein the adsorbent includes copper-plated iron or iron activated with platinum or palladium.

6. The composition of claim 1, wherein the adsorbent comprises at least one of activated carbon, vermiculite, alumina, a zeolite, and a char.

7. The composition of claim 1, wherein the energetic compound is an explosive that is a nitrocompound.

8. The composition of claim 1, wherein the energetic compound is a propellant.

9. The composition of claim 1, wherein the first bioremediation material includes bacteria, fungi, an aerobic microorganism, an anaerobic microorganism, an algae, a protozoa, or an actinomycetes.

10. The composition of claim 1, wherein the polymeric substance comprises a polyamide, a polysaccharide, a complex carbohydrate, a polymeric fatty acid, a polymer of an amino acid, or a protein.

11. The composition of claim 1, wherein the polymeric substance comprises at least one of starch and chitin.

12. The composition of claim 11, wherein the starch is a food grade starch.

13. A composition for removing energetic compounds from contaminated environments, comprising:
   an adsorbent including a magnesium-aluminum alloy;
   a first bioremediation material capable of degrading an energetic compound, wherein the energetic compound is an explosive;
   a polymer capable of fueling the first bioremediation material during the degrading of the energetic compound; and
   a second bioremediation material capable of breaking the polymer into a plurality of molecules over a degradation time period to provide the fueling of the first bioremediation material in a time-release manner.

14. The composition of claim 13, wherein the polymer comprises a polyamide, a polysaccharide, a complex carbohydrate, a polymeric fatty acid, a polymer of an amino acid, or a protein, wherein the polymer comprises at least one of starch and chitin, and wherein the adsorbent further comprises activated carbon, vermiculite, alumina, a zeolite, or a char.

15. The composition of claim 13, wherein the adsorbent comprises activated carbon impregnated with at least one metal and wherein the metal is chosen from the group consisting of: zero valent iron, zinc, tin, platinum, palladium, copper, manganese, iridium, cobalt, titanium, nickel, a magnesium-aluminum alloy, a ferro-titanium alloy, copper-plated iron, and iron activated with platinum or palladium.

16. The composition of claim 13, wherein the first bioremediation material includes bacteria, fungi, an aerobic microorganism, an anaerobic microorganism, an algae, a protozoa, or an actinomycetes and wherein the degradation time period is at least 20 days in length.

17. A composition for removing energetic compounds from contaminated environments, comprising:
   a first bioremediation material for degrading an energetic compound comprising an explosive or a propellant;
   a polymer for fueling the first bioremediation material during the degrading of the energetic compound, wherein the polymer comprises a polyamide, a polysaccharide, a complex carbohydrate, a polymeric fatty acid, a polymer of an amino acid, or a protein;

a second bioremediation material for breaking the polymer into a plurality of molecules over a degradation time period to provide the fueling of the first bioremediation material in a time-release manner; and a supported reactant comprising an adsorbent including activated carbon and a magnesium-aluminum alloy, wherein the degradation time period is at least 20 days in length.

18. The composition of claim 17, wherein the polymer comprises at least one of starch and chitin.

19. The composition of claim 17, wherein the first bioremediation material includes bacteria, fungi, an aerobic microorganism, an anaerobic microorganism, an algae, a protozoa, or an actinomycetes.

20. The composition of claim 17, wherein the activated carbon is impregnated with zero valent iron.

\* \* \* \* \*